United States Patent [19]

Orban

[11] Patent Number: 4,594,444

[45] Date of Patent: Jun. 10, 1986

[54] PROCESS FOR THE PREPARATION OF STERICALLY HINDERED HYDROXYPHENYLCARBOXYLIC ACID ESTERS

[75] Inventor: Ivan Orban, Basel, Switzerland

[73] Assignee: Ciba-Geigy Corporation, Ardsley, N.Y.

[21] Appl. No.: 680,681

[22] Filed: Dec. 12, 1984

[30] Foreign Application Priority Data

Dec. 22, 1983 [CH] Switzerland ............... 6857/83

[51] Int. Cl.$^4$ ................................. C07C 69/88
[52] U.S. Cl. ........................... 560/067; 560/75; 560/57; 560/65
[58] Field of Search .................... 560/67, 75

[56] References Cited

U.S. PATENT DOCUMENTS

| | | | |
|---|---|---|---|
| 3,330,859 | 7/1967 | Dexter | 560/67 |
| 3,779,945 | 12/1973 | Dexter | 560/67 |
| 4,417,071 | 11/1983 | Rosenberger | 560/67 |
| 4,536,593 | 8/1985 | Orban | 560/67 |

FOREIGN PATENT DOCUMENTS 1081789  8/1965  United Kingdom ............ 560/67

*Primary Examiner*—Paul J. Killos
*Attorney, Agent, or Firm*—Luther A. R. Hall

[57] ABSTRACT

If the transesterification of esters of the formula II

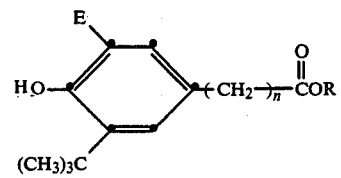

with alcohols of the formula III

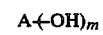

is catalyzed by treatment with catalytic amounts of an oxide or an organo-metallic compound of a metal of the fourth main group or subgroup of the periodic system, and if the resulting melt is then distilled in a flash distillation apparatus under specific conditions, compounds of the formula

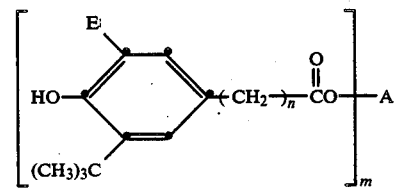

are obtained in a virtually quantitative yield. In the above formulae, R is methyl or ethyl, A is a radical of an m-hydric aliphatic alcohol, E is methyl or tert-butyl, m is 1 to 4 and n is 0 to 2. The products thus obtained do not contain any interfering by-products and do not have to be additionally purified. Reference is made to claim 1 regarding the meaning of the substituents and symbols R, A, B, m and n and also the distillation conditions.

7 Claims, No Drawings

PROCESS FOR THE PREPARATION OF STERICALLY HINDERED HYDROXYPHENYLCARBOXYLIC ACID ESTERS

The present invention relates to a process for the preparation of sterically hindered hydroxyphenylcarboxylic acid esters, in which a transesterification reaction is carried out by treatment with a metal oxide or an organometallic compound, and the resulting melt is distilled in a flash distillation apparatus.

Transesterification reactions for the preparation of sterically hindered hydroxyphenylcarboxylic acid esters are known. Thus, for example, German Auslegeschrift No. 1,201,349 and German Offenlegungsschrift No. 1,543,644 describe transesterification reactions of this type in which alkali metal alcoholates are employed as the catalysts. Transesterification reactions of the same type are catalysed by lithium amide in accordance with German Offenlegungsschrift No. 2,150,327. In all these processes by-products (in most cases oxidation products of 2,6-dialkylphenols) which, even in very small amounts, cause a drastic reduction in the stability on storage of the desired end product, are formed in varying small amounts. The indispensable removal of these by-products is expensive in terms of time, labour and energy.

It has now been found that carrying out the transesterification in the absence of a solvent, in the presence of catalytic amounts of an oxide or of an organometallic compound containing metals of the fourth main group or of the fourth subgroup of the periodic system, with subsequent distillation of the resulting melt in a flash distillation apparatus under specific conditions results, surprisingly, in a virtually quantitative yield of pure end product which, since it does not contain any interfering by-products, does not have to be additionally purified. A further advantage of this process is that the procedure is solvent-free.

The present invention relates, accordingly, to a process for the preparation of compounds of the formula I

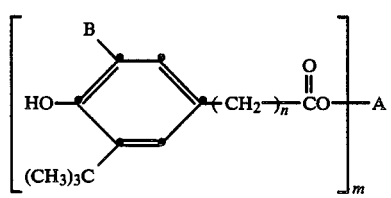

(I)

in which n is the numbers 0 to 2, m is the numbers 1 to 4, A is a radical which is derived from an m-hydric aliphatic alcohol and has 2 to 18 carbon atoms and B is methyl or t.-butyl, by transesterifying approx. m moles of an ester of the formula II

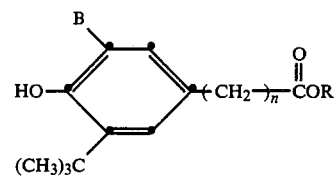

(II)

in which R is methyl or ethyl, with an alcohol of the formula III $$A\text{-(OH)}_m \quad (III)$$

which comprises (a) carrying out the transesterification in the presence of an oxide or an organometallic compound of a metal of the fourth main group or fourth subgroup of the periodic system, as catalyst, in an amount between 0.05 and 1.0 mol %, based on the ester of the formula II, and (b) distilling the resulting melt in a flash distillation apparatus under a pressure between 0.5 and 6 mbar, preferably between 1 and 3 mbar, and at a temperature between 230° and 270° C., preferably between 240° and 260° C., and granulating the resulting melt.

As a radical derived from an m-hydric aliphatic alcohol, A is an m-valent, substituted or unsubstituted, aliphatic radical having 2 to 18 carbon atoms.

If m is 1, A is $C_2$-$C_{18}$-alkyl, linear or branched, for example, ethyl, n-propyl, isopropyl, n-butyl, sec.-butyl, tert.-butyl, n-pentyl, n-hexyl, 2-ethylhexyl, n-octyl, 1,1,3,3-tetramethylbutyl, n-decyl, n-dodecyl, n-hexadecyl or n-octadecyl. n-Octadecyl is preferred.

If m is 2, A can be, for example, $C_2$-$C_{18}$-alkylene, preferably $C_2$-$C_6$-alkylene, such as dimethylene, trimethylene, tetramethylene, hexamethylene, 2,2-dimethyltrimethylene, octamethylene, nonamethylene, decamethylene, dodecamethylene or octadecamethylene. The alkylene group can be interrupted by —O—, —S— or —N(R)—, as in 2-thia-1,3-propylene, 3-thia-1,5-pentylene, 4-oxaheptamethylene, 3,6-dioxa-1,8-octamethylene or 3,6-diaza-1,8-octamethylene. If A is interrupted $C_2$-$C_6$-alkylene, it is preferably a group

If m is 3, A can be a trivalent, aliphatic $C_3H_5$ to $C_7H_{13}$ hydrocarbon radical, such as

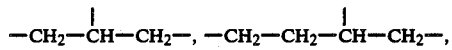

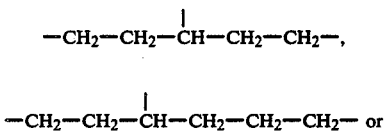

If m is 4, A can be a tetravalent, aliphatic $C_4H_6$ to $C_{10}H_{18}$ hydrocarbon radical, such as

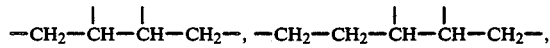

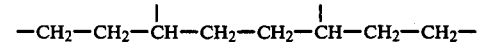

or preferably pentaerythrityl.

Examples of metal oxides which are suitable as catalysts are germanium dioxide and zirconium dioxide.

Examples of suitable organometallic compounds of a metal of the fourth main group or fourth subgroup of the periodic system are compounds of the formula IV $$(R_1O)_4{-}M \qquad (IV)$$

in which $R_1$ is $C_1{-}C_{18}$-alkyl, phenyl or benzyl and M is the element Ge, Zr, Sn or especially Ti, or, preferably, compounds of the formula V

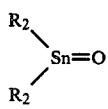

in which $R_2$ is $C_4{-}C_{12}$-alkyl.

Examples of $R_2$ as $C_4{-}C_{12}$-alkyl are n-butyl, n-pentyl, n-hexyl, n-octyl, n-decyl and n-dodecyl.

$R_1$ and $R_2$ are preferably n-butyl.

The catalyst is preferably employed in amounts between 0.1 and 0.3 mol %, based on the ester of the formula II, at temperatures between 110° and 220° C., particularly preferably between 120° and 200° C., and under a pressure between 250 and 3 mbar, for 2 to 5 hours.

In the case of compounds of the formula I in which m is >1, it is advisable to employ an excess of 10–30 mol % of the ester of the formula II.

Examples of suitable flash distillation apparatus are Filmtruders, falling-film evaporators and, in particular, thin-film evaporators. Distillation is advantageously carried out continuously, but a discontinuous procedure is also possible.

The melt obtained from the flash distillation only needs to be granulated by customary methods, for example on the cooling conveyor belt, in order to obtain the finished end product in a virtually pure, free-flowing, dust-free form, ready for its specific use.

The process according to the invention is particularly suitable for the preparation of compounds of the formula I by transesterifying an ester of the formula II with an alcohol of the formula III, n in the formulae I, II and III being the number 2 and m being the numbers 1, 2 or 4, A being $C_2{-}C_{18}$-alkyl if m=1, being $C_2{-}C_6$-alkylene, a group

if m=2, and being pentaerythrityl if m=4, and R being methyl.

The preferred process according to the invention is the preparation of pentaerythrityl tetrakis-[3-(3,5-di-tert.-butyl-4-hydroxyphenyl)-propionate] by transesterifying methyl 3-(3,5-di-tert.-butyl-4-hydroxyphenyl)-propionate with pentaerythritol, wherein (a) the transesterification is carried out in the presence of a compound of the formula V in which $R_2$ is as defined above, and (b) the resulting melt is distilled in a flash distillation apparatus under a pressure between 1 and 3 mbar and at a temperature between 240° and 260° C., and the melt obtained is granulated.

The esters of the formula II, the alcohols of the formula III and the catalysts are known substances. If individual members among these substances are new, they can be prepared by generally known processes.

The compounds of the formula I are valuable stabilisers for organic materials which are liable to decompose, for example synthetic organic polymers, animal and vegetable oils, hydrocarbons, lubricants and the like.

The following examples illustrate the invention without limiting it.

EXAMPLE 1

(a) 1533 g (5.25 moles) of methyl 3-(3,5-di-tert.-butyl-4-hydroxyphenyl)-propionate and 143 g (1.05 moles) of pentaerythritol are initially placed in a flask equipped with a dephlegmator heated at 80° C., and are warmed to 80° C. 2.1 g (0.0084 mole) of dibutyltin oxide are then added, and the mixture is heated at 180° C. under nitrogen and under a pressure of 250 mbar. In the course of this, the methanol formed is distilled off into the receiver. The distillation is continued for a further 45 minutes at 180° C. and 250 mbar, and the vacuum is then improved successively to approx. 4 mbar in the course of 1 hour. Finally, the mixture is stirred for a further 30 minutes at 180° C. and 3 to 4 mbar. The slightly yellowish melt obtained is cooled to 80°–100° C. and is kept under nitrogen until it is processed further.

(b) The melt obtained under (a) is passed, in portions of approx. 300 ml, through a thin-film evaporator under a pressure of 1–3 mbar and a temperature of 260° C. in the evaporator section. The temperature in the feed vessel and in the collecting vessel is 150° C. The throughput is from approx. 1000 g per hour at a rotor speed of approx. 50 r.p.m. In this process, the melt of the end product is collected in the collecting vessel, and the excess methyl 3-(3,5-di-tert.-butyl-4-hydroxyphenyl)-propionate, containing traces of methanol, is collected in the distillation receiver.

At the end of each run the vacuum in the apparatus is released by means of nitrogen, and the product melt is run out of the collecting vessel onto a metal sheet so that it may solidify. After solidification, the melt is comminuted. Under operating conditions, the melt is passed directly to the granulating stage. 1232 g (99.7% of theory) of pentaerythrityl tetrakis-[3-(3,5-di-tert.-butyl-4-hydroxyphenyl)-propionate] having a melting point of 58°–62° C. are obtained.

EXAMPLE 2

(a) 1051 g (3.6 moles) of methyl 3-(3,5-di-tert.-butyl-4-hydroxyphenyl)-propionate and 1001 g (3.7 moles) of stearyl alcohol are initially placed in a flask and warmed to 80° C. 1.8 g (0.0072 mole) of dibutyltin oxide are then added and the mixture is heated to 140° C. under nitrogen and under a pressure of 250 mbar. The methanol formed is distilled off in the course of this into the receiver. The vacuum is then improved successively to approx. 4 mbar at 140° C. in the course of 1 hour. Finally, the mixture is stirred for a further 30 minutes at 140° C. and 3–4 mbar. The slightly yellowish melt obtained is cooled to 80°–100° C. and is kept under nitrogen until it is processed further.

(b) The melt obtained under (a) is processed further exactly as described under Example 1(b).

1905 g (99.8% of theory) of stearyl 3-(3,5-di-tert.-butyl-4-hydroxyphenyl)-propionate having a melting point of 50°–51° C. are obtained.

EXAMPLE 3

The procedure of Example 2 is repeated, with the single exception that only 972 g (3.6 moles) of stearyl alcohol are employed instead of 1001 g.

1901 g (99.6% of theory) of stearyl 3-(3,5-di-tert.-butyl-4-hydroxyphenyl)-propionate having a melting point of 50°–51° C. are obtained.

EXAMPLE 4

The procedure of Example 1 is repeated, with the single exception that the transesterification is carried out at 190, instead of 180° C. The product of Example 1 is obtained, with the same melting point and in the same yield.

What is claimed is:

1. A process for the preparation of compounds of the formula I

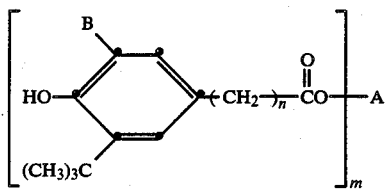

in which n is the numbers 0 to 2, m is the numbers 1 to 4, A is a radical which is derived from an m-hydric aliphatic alcohol and has 2 to 18 carbon atoms and B is methyl or t.-butyl, by transesterifying approx. m moles of an ester of the formula II

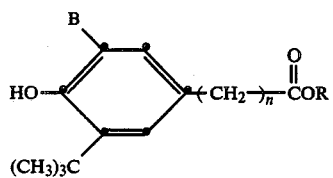

in which R is methyl or ethyl, with an alcohol of the formula III $$A(OH)_m \quad \text{(III)}$$

which comprises (a) carrying out the transesterification in the presence of an oxide or an organometallic compound of a metal of the fourth main group or fourth subgroup of the periodic system, as catalyst, in an amount between 0.05 and 1.0 mol %, based on the ester of the formula II, and (b) distilling the resulting melt in a flash distillation apparatus under a pressure between 0.5 and 6 mbar, and at a temperature between 230° and 270° C., and granulating the resulting melt.

2. A process according to claim 1, wherein the catalyst employed is a tin compound of the formula V

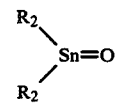

in which $R_2$ is $C_4$–$C_{18}$-alkyl.

3. A process according to claim 2, wherein the compound of the formula V is dibutyltin oxide.

4. A process according to claim 1 for the preparation of compounds of the formula I by transesterifying an ester of the formula II with an alcohol of the formula III, wherein, in the formulae I, II and III, n is the number 2 and m is the numbers 1, 2 or 4, A is $C_2$–$C_{18}$-alkyl if m=1, A is $C_2$–$C_6$-alkylene, a group $$-(CH_2)_z-S-(CH_2)_z- \text{ or } -(CH_2)_z-O-(CH_2)_z-O-(CH_2)_z-$$

if m=2, and A is pentaerythrityl if m=4, and R is methyl.

5. A process according to claim 1, wherein the catalyst in the transesterification is employed in amounts between 0.1 and 0.3 mol %, based on the ester of the formula II, at temperatures between 110° and 220° C. and under a pressure between 250 and 3 mbar.

6. A process according to claim 1, wherein the distillation of the melt in the flash distillation apparatus is carried out under a pressure between 1 and 3 mbar and at a temperature between 240° and 260° C.

7. A process according to claim 1, for the preparation of pentaerythrityl tetrakis-[3-(3,5-di-tert.-butyl-4-hydroxyphenyl)-propionate] by transesterifying methyl 3-(3,5-di-tert.-butyl-4-hydroxyphenyl)-propionate with pentaerythritol.

* * * * *